(12) United States Patent
Beard et al.

(10) Patent No.: US 8,614,326 B2
(45) Date of Patent: Dec. 24, 2013

(54) THERAPEUTIC QUINOLINE AND NAPHTHALENE DERIVATIVES

(75) Inventors: Richard L. Beard, Newport Beach, CA (US); Haiqing Yuan, Irvine, CA (US); John E. Donello, Dana Point, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 372 days.

(21) Appl. No.: 12/674,180

(22) PCT Filed: Aug. 21, 2008

(86) PCT No.: PCT/US2008/073798
§ 371 (c)(1),
(2), (4) Date: Oct. 22, 2010

(87) PCT Pub. No.: WO2009/026408
PCT Pub. Date: Feb. 26, 2009

(65) Prior Publication Data
US 2011/0046177 A1 Feb. 24, 2011

Related U.S. Application Data

(60) Provisional application No. 60/957,281, filed on Aug. 22, 2007.

(51) Int. Cl.
*C07D 215/38* (2006.01)

(52) U.S. Cl.
USPC ........................................... 546/159

(58) Field of Classification Search
USPC .......................................... 546/159; 514/312
See application file for complete search history.

(56) References Cited

U.S. PATENT DOCUMENTS

| | | | |
|---|---|---|---|
| 6,376,670 B1 | 4/2002 | Cuny et al. | |
| 2004/0167181 A1 | 8/2004 | Solow-Cordero | |
| 2008/0306058 A1* | 12/2008 | Billich et al. | 514/230.5 |
| 2012/0172386 A1* | 7/2012 | Billich et al. | 514/275 |

FOREIGN PATENT DOCUMENTS

| WO | WO2004/080463 | 9/2004 |
|---|---|---|
| WO | WO2007/031265 | 3/2007 |

OTHER PUBLICATIONS

Willis, J Med Chem, vol. 48(18), pp. 5813-5822, 2005.*
Marrero-Ponce, Bioorganic & Med Chem, 13(8), pp. 2881-2899, 2005.*
Marrero-Ponce, J Mol Modeling, 12(3), pp. 255-271, 2006.*
Means, Cardiovascular Research, VOl 82, pp. 193-200, 2009.*
Richard B. Silverman, "Prodrugs and Drug Delivery Systems,", *Organic Chemistry of Drug Design and Drug Action*, 2d Ed., Elsevier Academic Press: Amsterdam, 2004, pp. 496-557.
Chamontin, et. al. (Tetrahedron 55 (1999) 5821-5830).

* cited by examiner

*Primary Examiner* — D M Seaman
(74) *Attorney, Agent, or Firm* — Krishna Banerjee; Debra D. Condino

(57) ABSTRACT

Disclosed herein is a stable compound having a structure formula (I): therapeutic methods, compositions, and medicaments related thereto are also disclosed.

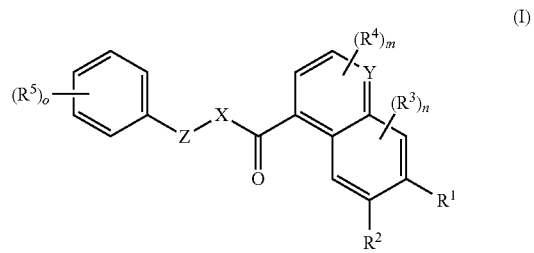

14 Claims, No Drawings

THERAPEUTIC QUINOLINE AND NAPHTHALENE DERIVATIVES

CROSS REFERENCE TO RELATED APPLICATIONS

This is a national stage application under 35 U.S.C. 371 of PCT patent application PCT/US 2008/073798, filed on Aug. 21, 2008, which claims the benefit of U.S. Provisional Patent Application 60/957,281 filed Aug. 22, 2007, each of which is hereby incorporated by reference in its entirety.

BACKGROUND

Sphingosine is a compound having the chemical structure shown in the general formula described below, in which $Y^1$ is hydrogen. It is known that various sphingolipids, having sphingosine as a constituent, are widely distributed in the living body including on the surface of cell membranes of cells in the nervous system.

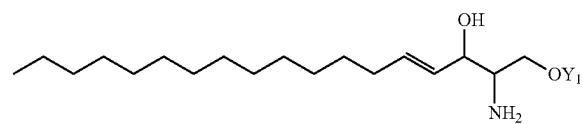

A sphingolipid is one of the lipids having important roles in the living body. A disease called lipidosis is caused by accumulation of a specified sphingolipid in the body. Sphingolipids present on cell membranes function to regulate cell growth; participate in the development and differentiation of cells; function in nerves; are involved in the infection and malignancy of cells; etc. Many of the physiological roles of sphingolipids remain to be solved. Recently the possibility that ceramide, a derivative of sphingosine, has an important role in the mechanism of cell signal transduction has been indicated, and studies about its effect on apoptosis and cell cycle have been reported.

Sphingosine-1-phosphate is an important cellular metabolite, derived from ceramide that is synthesized de novo or as part of the sphingomeyeline cycle (in animals cells). It has also been found in insects, yeasts and plants.

The enzyme, ceramidase, acts upon ceramides to release sphingosine, which is phosphorylated by sphingosine kinase, a ubiquitous enzyme in the cytosol and endoplasmic reticulum, to form sphingosine-1-phosphate. The reverse reaction can occur also by the action of sphingosine phosphatases, and the enzymes act in concert to control the cellular concentrations of the metabolite, which concentrations are always low. In plasma, such concentration can reach 0.2 to 0.9 µM, and the metabolite is found in association with the lipoproteins, especially the HDL. It should also be noted that sphingosine-1-phosphate formation is an essential step in the catabolism of sphingoid bases.

Like its precursors, sphingosine-1-phosphate is a potent messenger molecule that perhaps uniquely operates both intra- and inter-cellularly, but with very different functions from ceramides and sphingosine. The balance between these various sphingolipid metabolites may be important for health. For example, within the cell, sphingosine-1-phosphate promotes cellular division (mitosis) as opposed to cell death (apoptosis), which it inhibits. Intracellularly, it also functions to regulate calcium mobilization and cell growth in response to a variety of extracellular stimuli. Current opinion appears to suggest that the balance between sphingosine-1-phosphate and ceramide and/or sphingosine levels in cells is critical for their viability. In common with the lysophospholipids, especially lysophosphatidic acid, with which it has some structural similarities, sphingosine-1-phosphate exerts many of its extra-cellular effects through interaction with five specific G protein-coupled receptors on cell surfaces. These are important for the growth of new blood vessels, vascular maturation, cardiac development and immunity, and for directed cell movement.

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular disease. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

Fungi and plants have sphingolipids and the major sphingosine contained in these organisms has the formula described below. It is known that these lipids have important roles in the cell growth of fungi and plants, but details of the roles remain to be solved.

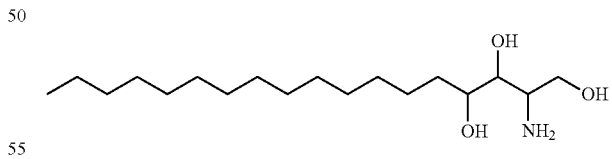

Recently it has been known that derivatives of sphingolipids and their related compounds exhibit a variety of biological activities through inhibition or stimulation of the metabolism pathways. These compounds include inhibitors of protein kinase C, inducers of apoptosis, immuno-suppressive compounds, antifungal compounds, and the like. Substances having these biological activities are expected to be useful compounds for various diseases.

DESCRIPTION OF THE INVENTION

Disclosed herein is a stable compound having a structure:

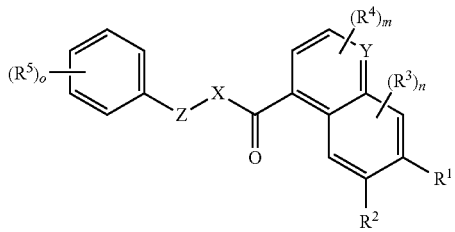

wherein n is 0, 1, or 2;

m is 1 or 2;

o is from 0 to 5;

one of $R^1$ and $R^2$ has a formula $C_{1-9}H_{0-23}N_{0-4}O_{0-4}S_{0-4}F_{0-6}Cl_{0-4}Br_{0-4}I_{0-4}$, and is selected from: a substituted or unsubstituted heterocycle having 5 or 6 atoms in the ring; and Cy, —S-Cy, —NH-Cy, and —O-Cy, wherein Cy is a substituted or unsubstituted carbocycle or a substituted or unsubstituted heterocycle;

one of $R^1$ and $R^2$ is hydrogen or a substituent having a formula $C_{0-12}H_{0-26}N_{0-2}O_{0-4}S_{0-1}P_{0-1}F_{0-6}Cl_{0-1}Br_{0-1}I_{0-1}$;

each $R^3$, $R^4$, and $R^5$ are independently a substituent having a formula $C_{0-12}H_{0-26}N_{0-2}O_{0-4}S_{0-1}P_{0-1}F_{0-6}Cl_{0-1}Br_{0-1}I_{0-1}$;

Y is N or C—H or C—$R^4$;

X is O, S, NH, N-alkyl having from 1 to 4 carbon atoms, or a bond; and

Z is hydrocarbyl having a formula $C_{1-8}H_{4-17}$.

These compounds are useful for the treatment of diseases or conditions such as glaucoma, dry eye, angiogenesis, cardiovascular conditions and diseases, wounds, and pain. The compound is incorporated into a dosage form or a medicament and administered to the mammal, such as a person, in need thereof. Different types of suitable dosage forms and medicaments are well known in the art, and can be readily adapted for delivery of the compounds disclosed herein.

For the purposes of this disclosure, "treat," "treating," or "treatment" refer to the use of a compound, composition, therapeutically active agent, or drug in the diagnosis, cure, mitigation, treatment, or prevention of disease or other undesirable condition.

Stable means that a compound is sufficiently stable to be stored in a bottle at room temperature under a normal atmosphere for at least 12 hours, or stable enough to be useful for any purpose disclosed herein.

Unless otherwise indicated, reference to a compound should be construed broadly to include pharmaceutically acceptable salts, prodrugs, tautomers, alternate solid forms, non-covalent complexes, and combinations thereof, of a chemical entity of the depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

A prodrug is a compound which is converted to a therapeutically active compound after administration. For example, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject.

Tautomers are isomers that are in rapid equilibrium with one another. For example, tautomers may be related by transfer of a proton, hydrogen atom, or hydride ion.

Unless stereochemistry is explicitly depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

Heterocycle is a substituted or unsubstituted ring having at least one atom in the ring selected from N, O, and S. A heterocycle may be aromatic or non aromatic. An aromatic heterocycle is also called heteroaryl.

Carbocycle is a substituted or unsubstituted ring wherein all of the atoms in the ring are carbon. Examples include phenyl, cycloalkyl, such as cyclopropyl, cyclobutyl, cyclopentyl, cyclohexyl, cyclopentenyl, cyclohexenyl, etc.

A substituted ring or moiety means that a hydrogen is replaced with a substituent. For example, a substituted carbocycle or heterocycle has a substituent directly attached to the ring instead of hydrogen.

$R^1$, $R^2$, $R^3$, $R^4$, and $R^5$ are all substituents. Examples of substituents may include the following subject to the constraints defined herein for that particular moiety or substituent:

A. Hydrocarbyl, meaning a moiety consisting of carbon and hydrogen only, including, but not limited to:
1. alkyl, such as:
    linear alkyl, i.e. a moiety consisting of carbon and hydrogen having no double bonds, e.g. methyl, ethyl, n-propyl, n-butyl, n-pentyl, n-hexyl, etc.,
    branched alkyl, e.g. iso-propyl, t-butyl and other branched butyl isomers, branched pentyl isomers, etc.,
    cycloalkyl, e.g. cyclopropyl, cyclobutyl, cyclopentyl, cyclohexyl, etc.,
    combinations of linear, branched, and/or cycloalkyl;
2. alkenyl, e.g. hydrocarbyl having 1 or more double bonds, including linear, branched, or cycloalkenyl
3. alkynyl, e.g. hydrocarbyl having 1 or more triple bonds, including linear, branched, or cycloalkynyl;
4. combinations of alkyl, alkenyl, and/or akynyl B. alkyl-CN, such as —$CH_2$—CN, —$(CH_2)_2$—CN; —$(CH_2)_3$—CN, and the like;

C. Hydroxy, —OH

D. hydroxyalkyl, i.e. alkyl-OH, such as hydroxymethyl, hydroxyethyl, and the like;

E. ether substituents, including —O-alkyl, alkyl-O-alkyl, and the like;

F. thioether substituents, including —S-alkyl, alkyl-S-alkyl, and the like;
G. amine substituents, including —NH$_2$, —NH-alkyl, —N-alkyl$^1$alkyl$^2$ (i.e., alkyl$^1$ and alkyl$^2$ are the same or different, and both are attached to N), alkyl-NH$_2$, alkyl-NH-alkyl, alkyl-N-alkyl$^1$alkyl$^2$, and the like;
H. aminoalkyl, meaning alkyl-amine, such as aminomethyl (—CH$_2$-amine), aminoethyl, and the like;
I. ester substituents, including —CO$_2$-alkyl, —CO$_2$-phenyl, etc.;
J. other carbonyl substituents, including aldehydes; ketones, such as acyl, including, acetyl, propionyl, and benzoyl substituents are contemplated;
K. fluorocarbons or hydroflourocarbons such as —CF$_3$, —CH$_2$CF$_3$, etc.; and
L. other nitrogen containing substituents such as —CN and —NO$_2$,
M. other sulfur containing substitutents such as sulfide, sulfonyl or sulfoxide;
N. aryl;
O. combinations of the above are also possible, subject to the constraints defined;
P. Alternatively, a substituent may be —F, —Cl, —Br, or —I.

In one embodiment, R$^1$, R$^2$, R$^3$, R$^4$, and R$^5$ are moieties having no Cl, Br, or I, unless the Cl, Br, or I is attached directly to a carbon of an aromatic ring. In other words, if R$^1$, R$^2$, R$^3$, R$^4$, or R$^5$ contain Cl, Br, or I, the moiety either consists of —Cl, —Br, or —I; or is an aromatic or heteroaromatic ring having —Cl, —Br, or —I directly bonded to a carbon atom of the ring.

Aryl is any substituted or unsubstituted aromatic or heteroaromatic ring or ring system. Some examples of aryl include substituted or unsubstituted benzenes, pyridines, pyrazines, pyridazines, pyrimidines, triazines, thiophenes, furans, thiazoles, thiadiazoles, isothiazoles, oxazoles, oxadiazoles, isooxazoles, naphthalenes, quinolines, tetralins, chromans, thiochromans, tetrahydroquinolines, dihydronaphthalenes, tetrahydronaphthalenes, chromenes, thiochromenes, dihydroquinolines, indans, dihydrobenzofurans, dihydrobenzothiophenes, indenes, benzofurans, benzothiophenes, coumarins, coumarinones, and the like.

Hydrocarbyl substituted methylene is

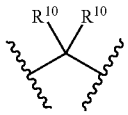

where each R10 is independently H or hydrocarbyl.

The formula C$_{1-9}$H$_{0-23}$N$_{0-4}$O$_{0-4}$S$_{0-4}$F$_{0-6}$Cl$_{0-4}$Br$_{0-4}$I$_{0-4}$ means that the moiety of that formula is composed of the following atoms:
from 1 to 9 carbon atoms;
from 0 to 23 hydrogen atoms;
from 0 to 4 nitrogen atoms;
from 0 to 4 oxygen atoms;
from 0 to 4 sulfur atoms;
from 0 to 6 fluorine atoms;
from 0 to 4 chlorine atoms;
from 0 to 4 bromine atoms; and
from 0 to 4 iodine atoms.

Similarly, the formula C$_{0-12}$H$_{0-26}$N$_{0-2}$O$_{0-4}$S$_{0-1}$P$_{0-1}$F$_{0-6}$Cl$_{0-1}$Br$_{0-1}$I$_{0-1}$ means that the moiety of that formula is composed of the following atoms:
from 0 to 12 carbon atoms;
from 0 to 26 hydrogen atoms;
0 or 2 nitrogen atoms;
from 0 to 4 oxygen atoms;
0 or 1 sulfur atoms;
0 or 1 phosporous atoms;
from 0 to 6 fluorine atoms;
0 or 1 chlorine atoms;
0 or 1 bromine atoms; and
0 or 1 iodine atoms.

Similarly, the formula C$_{1-8}$H$_{4-17}$ means that the moiety of that formula is composed of the following atoms:
from 1 to 8 carbon atoms; and
from 4 to 17 hydrogen atoms;

If a chemical species is an ion, only the atoms covalently attached to other atoms of a formula are counted. For example, if the species is a carboxylate associated with a sodium counter-ion, the sodium is not counted as part of the formula, or if the species is an ammonium ion associated with a chloride counter-ion, the chlorine is not counted as part of the formula.

In one embodiment, n is 0.
In another embodiment, n is 1.
In another embodiment, n is 2.
In another embodiment, m is 1.
In another embodiment, m is 2.
In another embodiment, o is 0.
In another embodiment, o is 1.
In another embodiment, o is 2.
In another embodiment, o is 3.
In another embodiment, o is 4.
In another embodiment, o is 5.

In one embodiment, an R$^5$ is a straight or branched chain alkyl, aryl, alkenyl, alkynyl, halo, haloalkyl, hydroxyl, alkoxy, alkylhydroxy (-alkyl-OH), alkylcarbonyl (—C(O)-alkyl), formyl, oxycarbonyl (—OC(O)-hydrocarbyl), carboxyl, alkyl carboxylate (—CO$_2$-alkyl), alkyl amide, aminocarbonyl (—NR$_2$C(O)-hydrocarbyl, where R is hydrocarbyl), amino, cyano, diazo, nitro, phosphate, thio, sulfoxyl (—S(O)-hydrocarbyl), or sulfonyl (—S(O)$_2$-hydrocarbyl).

In another embodiment, each R$^5$ is independently a straight or branched chain alkyl, aryl, alkenyl, alkynyl, halo, haloalkyl, hydroxyl, alkoxy, alkylhydroxy (-alkyl-OH), alkylcarbonyl (—C(O)-alkyl), formyl, oxycarbonyl (—OC(O)-hydrocarbyl), carboxyl, alkyl carboxylate (—CO$_2$-alkyl), alkyl amide, aminocarbonyl (—NR$_2$C(O)-hydrocarbyl, where R is hydrocarbyl), amino, cyano, diazo, nitro, phosphate, thio, sulfoxyl (—S(O)-hydrocarbyl), or sulfonyl (—S(O)$_2$-hydrocarbyl).

In another embodiment, an R$^3$ is a straight or branched chain alkyl, aryl, alkenyl, alkynyl, halo, haloalkyl, hydroxyl, alkoxy, alkylhydroxy, alkylcarbonyl, formyl, oxycarbonyl, carboxyl, alkyl carboxylate, alkyl amide, aminocarbonyl, amino, cyano, diazo, nitro, phosphate, thio, sulfoxyl, sulfonyl, or a group selected from:

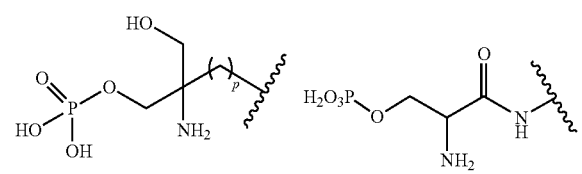

-continued

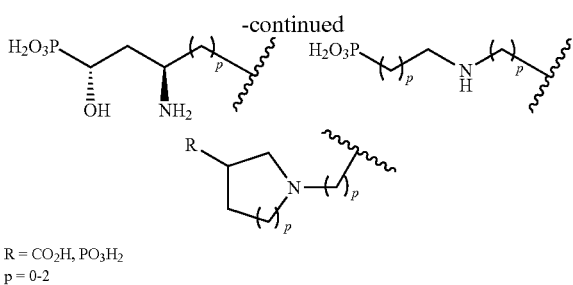

R = CO₂H, PO₃H₂
p = 0-2

In another embodiment, each R³ is a straight or branched chain alkyl, aryl, alkenyl, alkynyl, halo, haloalkyl, hydroxyl, alkoxy, alkylhydroxy, alkylcarbonyl, formyl, oxycarbonyl, carboxyl, alkyl carboxylate, alkyl amide, aminocarbonyl, amino, cyano, diazo, nitro, phosphate, thio, sulfoxyl, sulfonyl, or a group selected from:

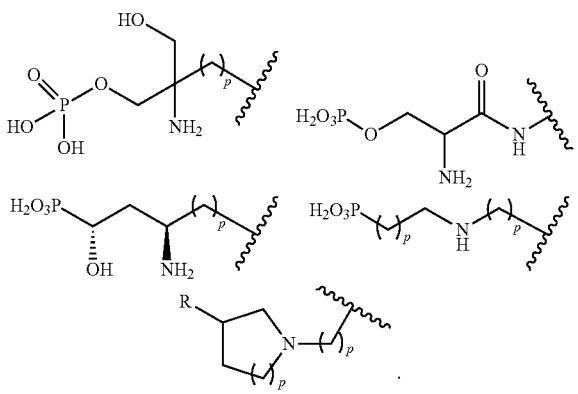

R = CO₂H, PO₃H₂
p = 0-2

In another embodiment, an R⁴ is a straight or branched chain alkyl, aryl, alkenyl, alkynyl, halo, haloalkyl, hydroxyl, alkoxy, alkylhydroxy, alkylcarbonyl, formyl, oxycarbonyl, carboxyl, alkyl carboxylate, alkyl amide, aminocarbonyl, amino, cyano, diazo, nitro, phosphate, thio, sulfoxyl, sulfonyl, or a group selected from:

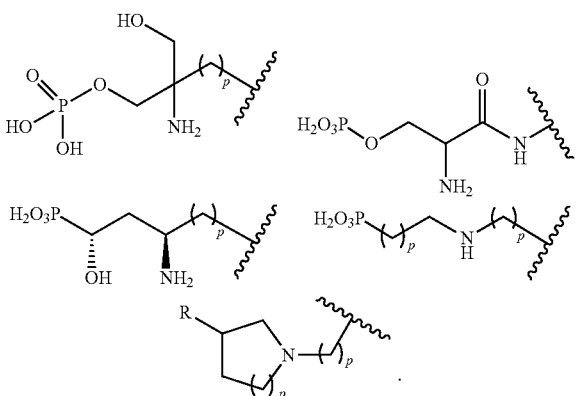

R = CO₂H, PO₃H₂
p = 0-2

In another embodiment, each R⁴ is a straight or branched chain alkyl, aryl, alkenyl, alkynyl, halo, haloalkyl, hydroxyl, alkoxy, alkylhydroxy, alkylcarbonyl, formyl, oxycarbonyl, carboxyl, alkyl carboxylate, alkyl amide, aminocarbonyl, amino, cyano, diazo, nitro, phosphate, thio, sulfoxyl, sulfonyl, or a group selected from:

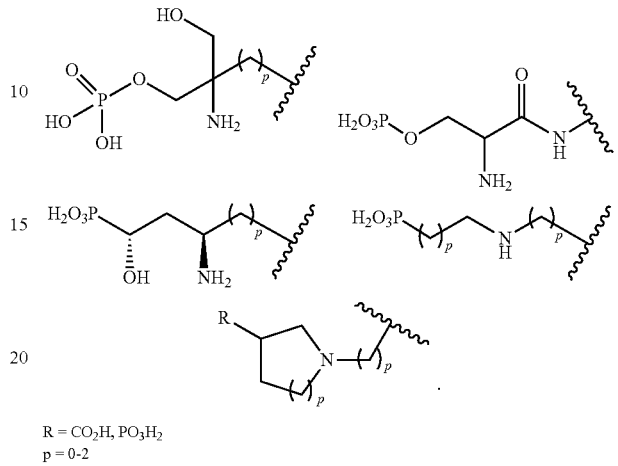

R = CO₂H, PO₃H₂
p = 0-2

$R^1$ and $R^2$ are different. One of the two one of $R^1$ and $R^2$ has a formula $C_{1-9}H_{0-23}N_{0-4}O_{0-4}S_{0-4}F_{0-6}Cl_{0-4}Br_{0-4}I_{0-4}$, and is selected from: a substituted or unsubstituted heterocycle having 5 or 6 atoms in the ring; and Cy, —S-Cy, —NH-Cy, and —O-Cy, wherein Cy is a substituted or unsubstituted carbocycle or a substituted or unsubstituted heterocycle.

The other $R^1$ and $R^2$ is hydrogen, or is subject to the same constraints as $R^3$, $R^4$, and $R^5$.

In other words, the structures below are contemplated, where q is from 0 to 3, Hy is a substituted or unsubstituted heterocycle having 5 or 6 atoms in the ring, and Hy, Cy, —S-Cy, —NH-Cy, and —O-Cy have the formula $C_{1-9}H_{0-23}N_{0-4}O_{0-4}S_{0-4}F_{0-6}Cl_{0-4}Br_{0-4}I_{0-4}$.

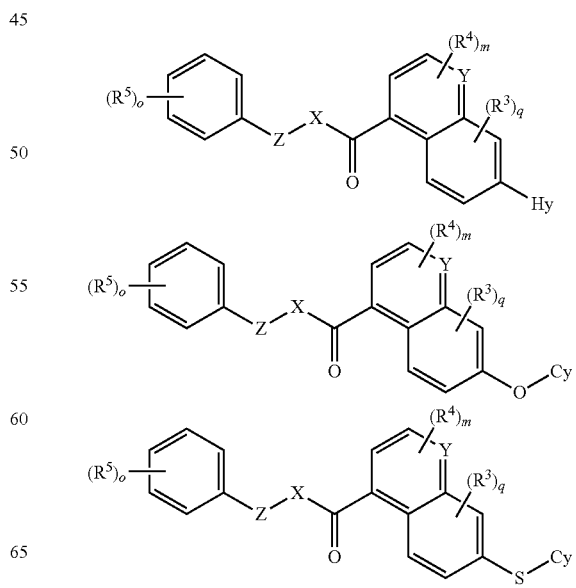

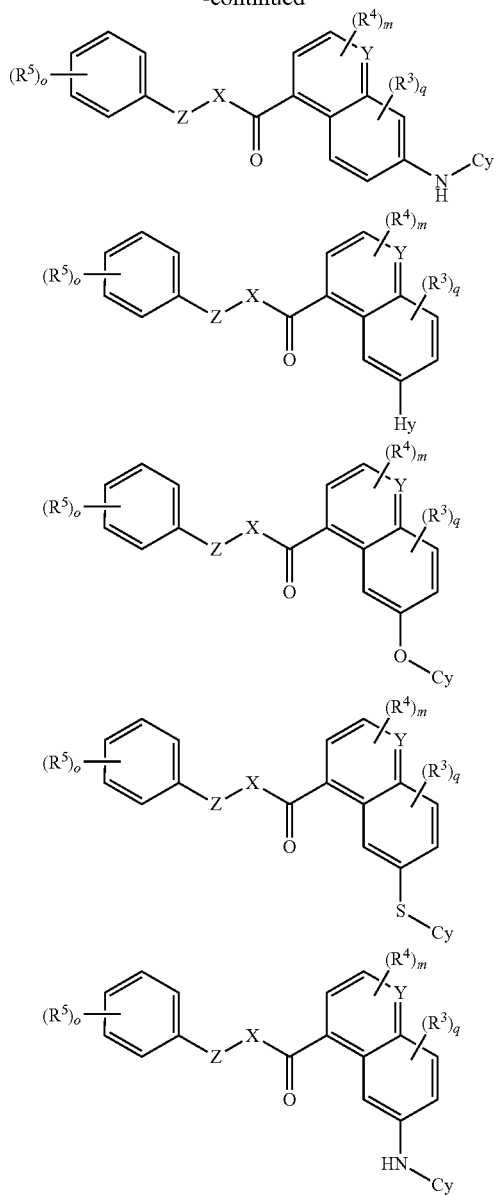

Some examples of Hy include the following:

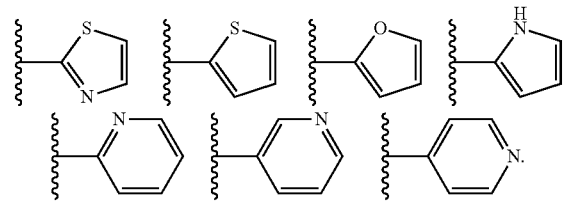

Some examples of Cy include the following:

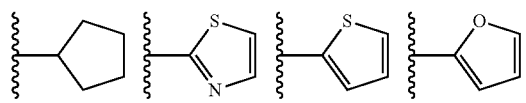

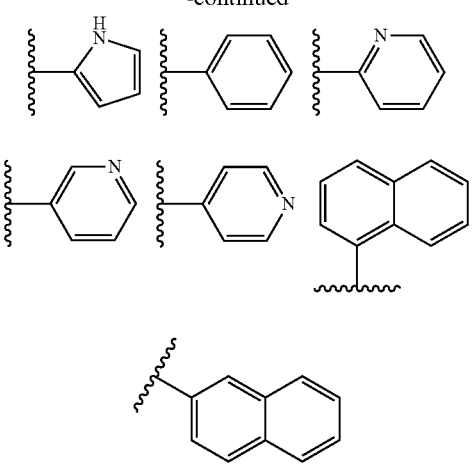

In one embodiment, one of $R^1$ and $R^2$ has a formula $C_{1-9}H_{0-23}N_{0-4}O_{0-4}S_{0-4}F_{0-6}$, and is selected from: a substituted or unsubstituted heterocycle having 5 or 6 atoms in the ring; and Cy, —S-Cy, —NH-Cy, and —O-Cy, wherein Cy is a substituted or unsubstituted carbocycle or a substituted or unsubstituted heterocycle.

Y is N, C—H or C—$R^4$. Thus, compounds having structures such as those below are contemplated.

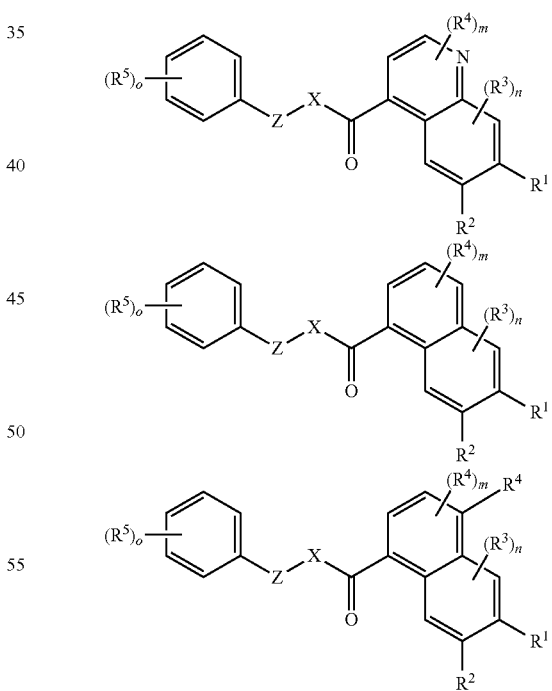

X is O, S, NH, N-alkyl having from 1 to 4 carbon atoms, or a bond. Thus, compounds having structures such as those below are contemplated.

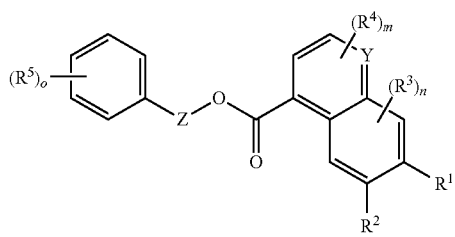

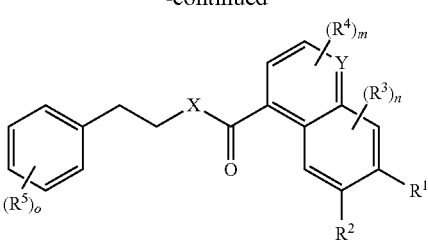

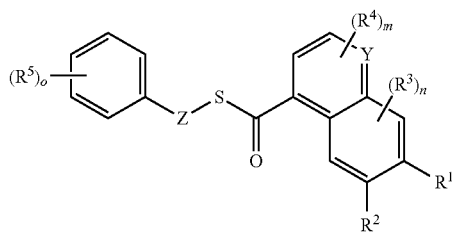

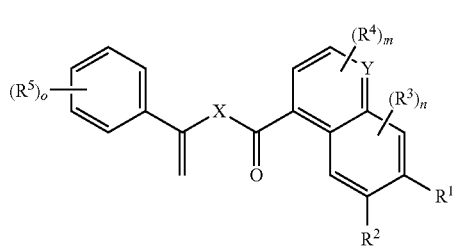

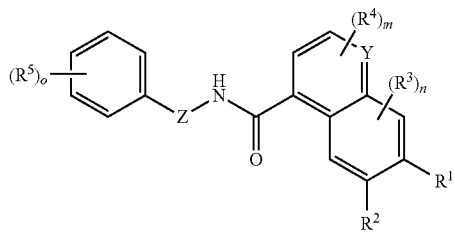

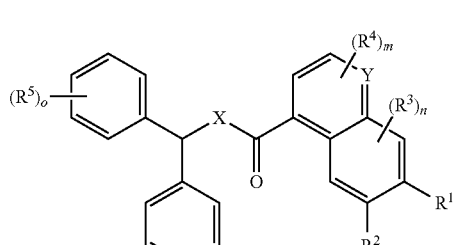

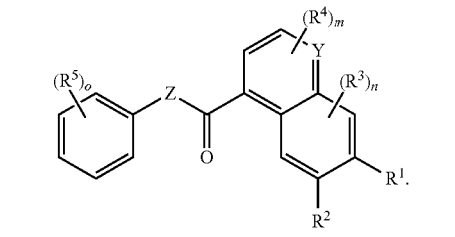

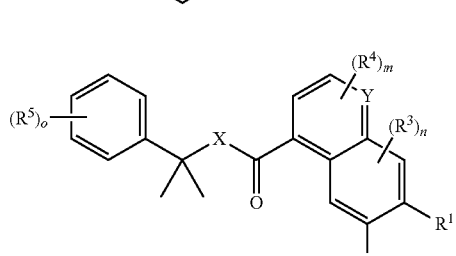

Z is hydrocarbyl having a formula $C_{1-8}H_{4-17}$. Thus, compounds having structures such as those below are contemplated.

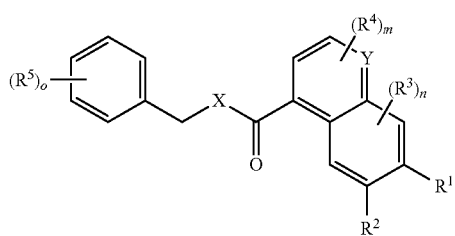

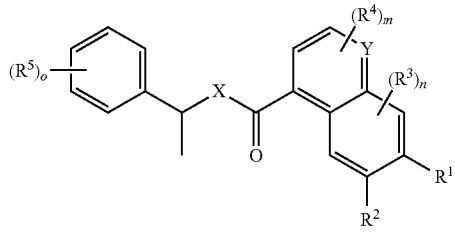

In one embodiment, Z is $C_{1-8}$ alkyl.

One embodiment is a compound represented by the structure:

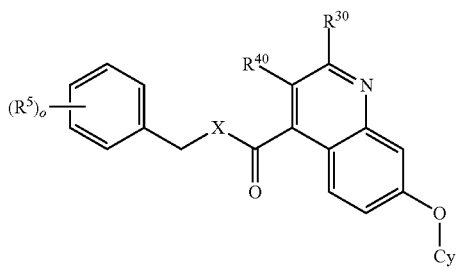

wherein $R^{30}$ is phenyl, heteroaryl, or t-butyl;

$R^{40}$ is $C_{1-6}$ alkyl, $C_{1-7}$ carboxylate, or $C_{1-7}$ alkylcarbonyl; and Cy is a substituted or unsubstituted carbocycle or a substituted or unsubstituted heterocycle.

Compounds according to one of the structures below, wherein $R^{20}$ is C1-6 alkyl, are contemplated.

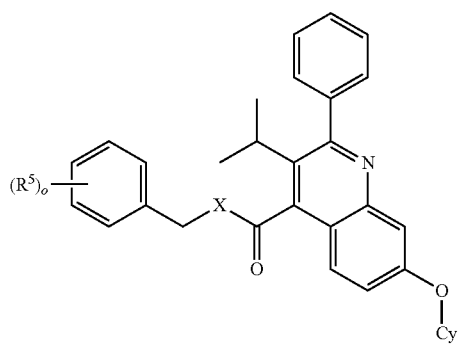
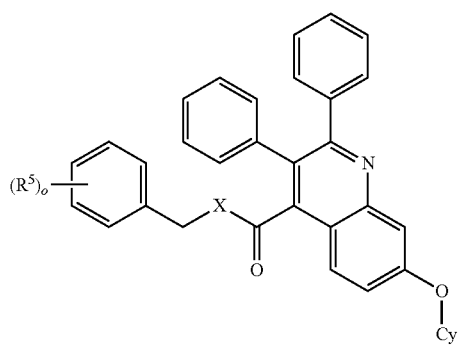
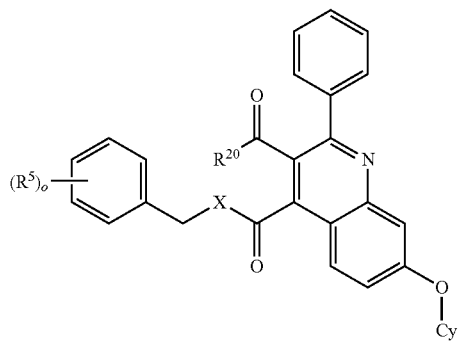
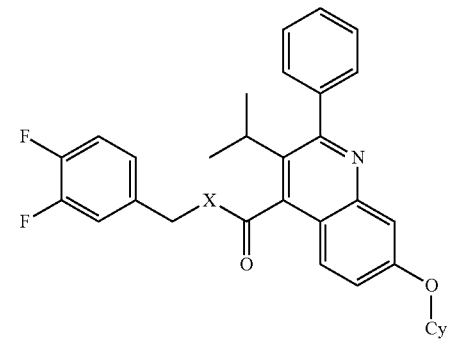
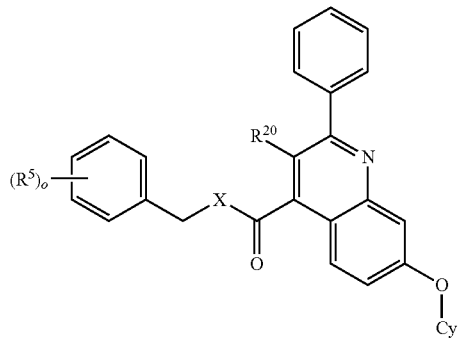
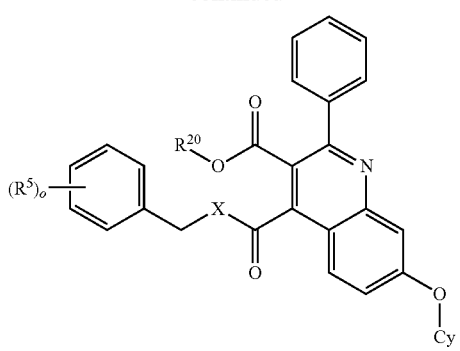
Hypothetical examples of useful compounds are shown below.
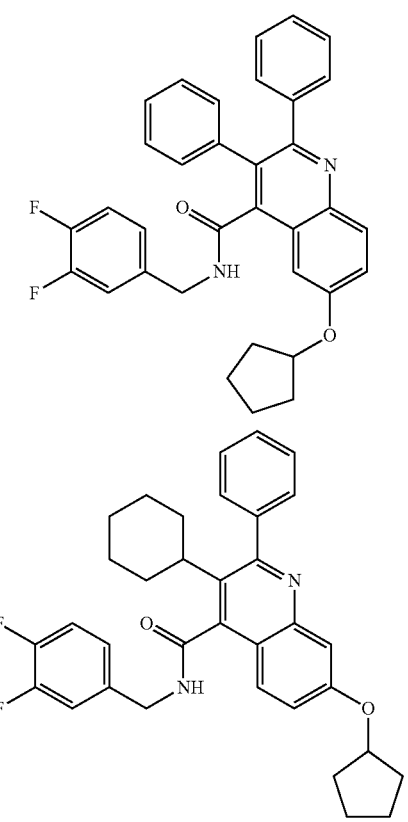
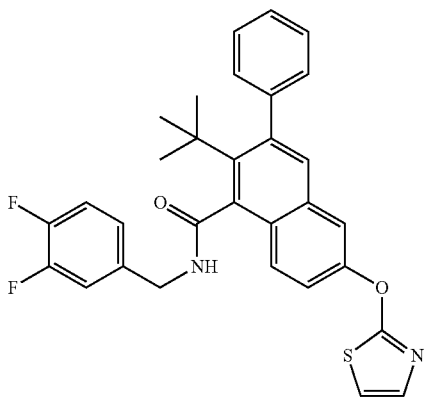

15
-continued
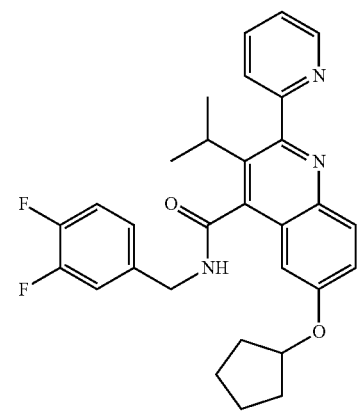
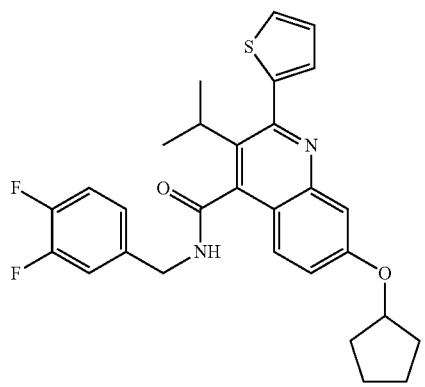
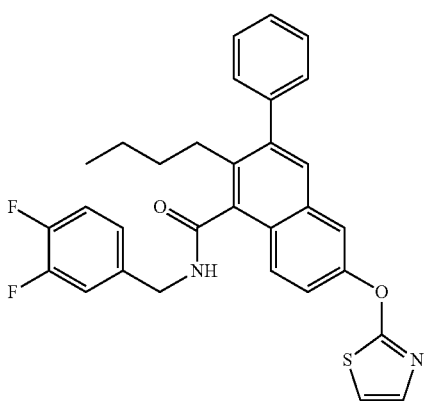
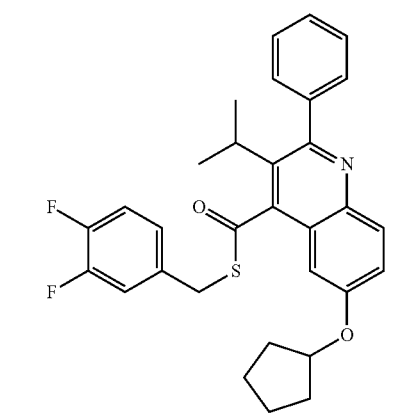
16
-continued
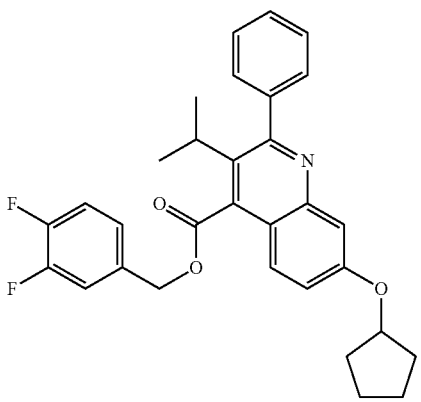
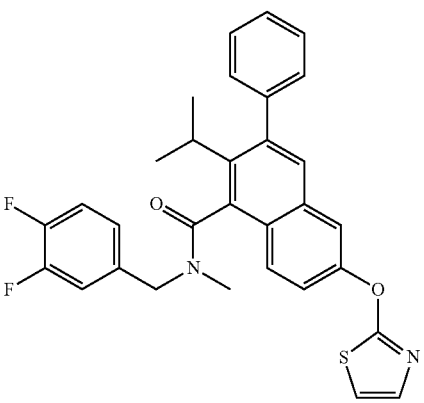
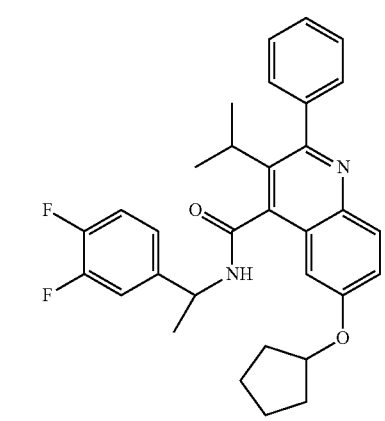
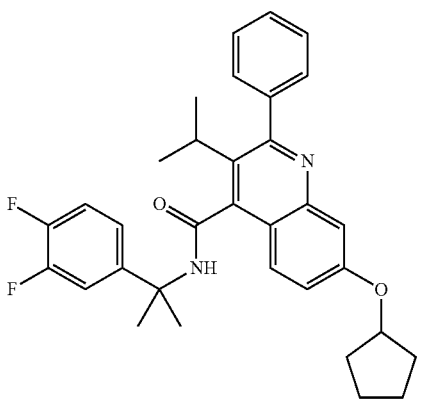

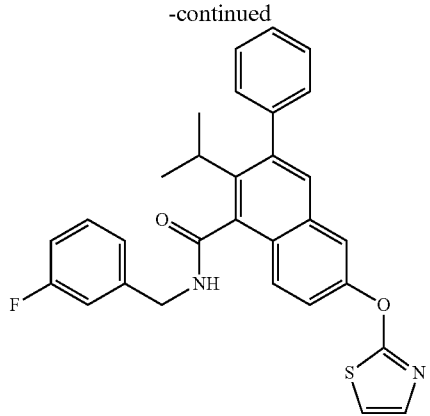
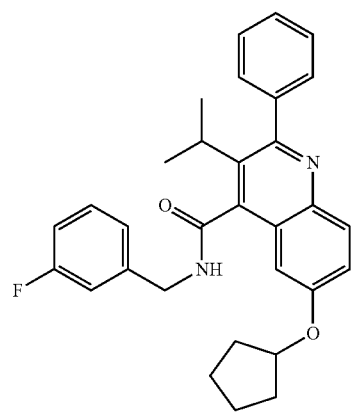
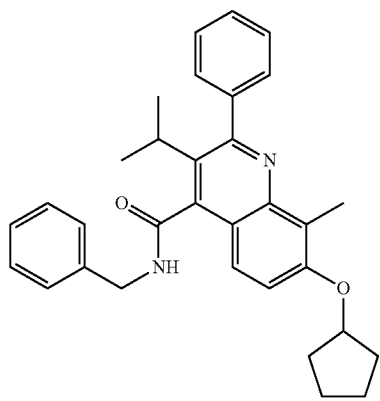
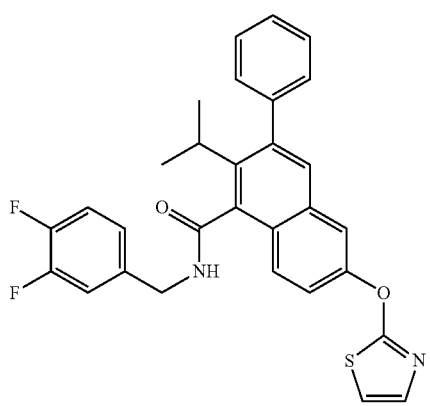
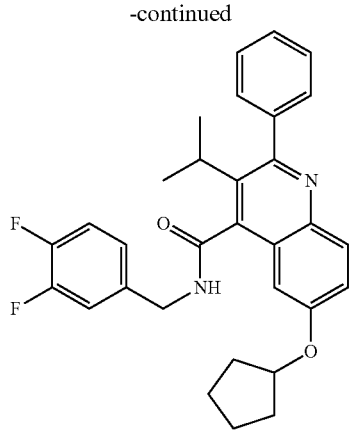
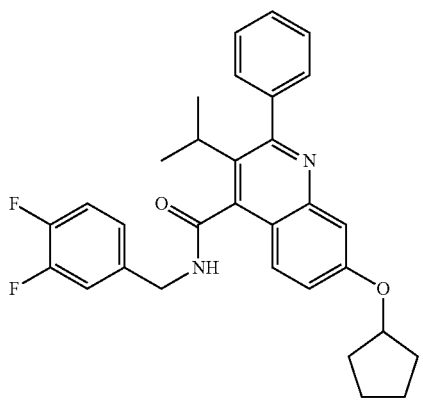
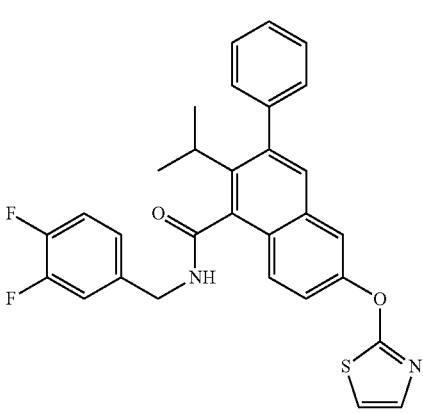
On example of a general method to prepare these compounds is described in Scheme 1.
Scheme 1
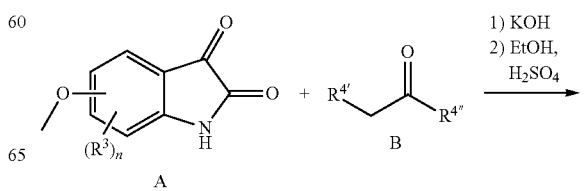

-continued

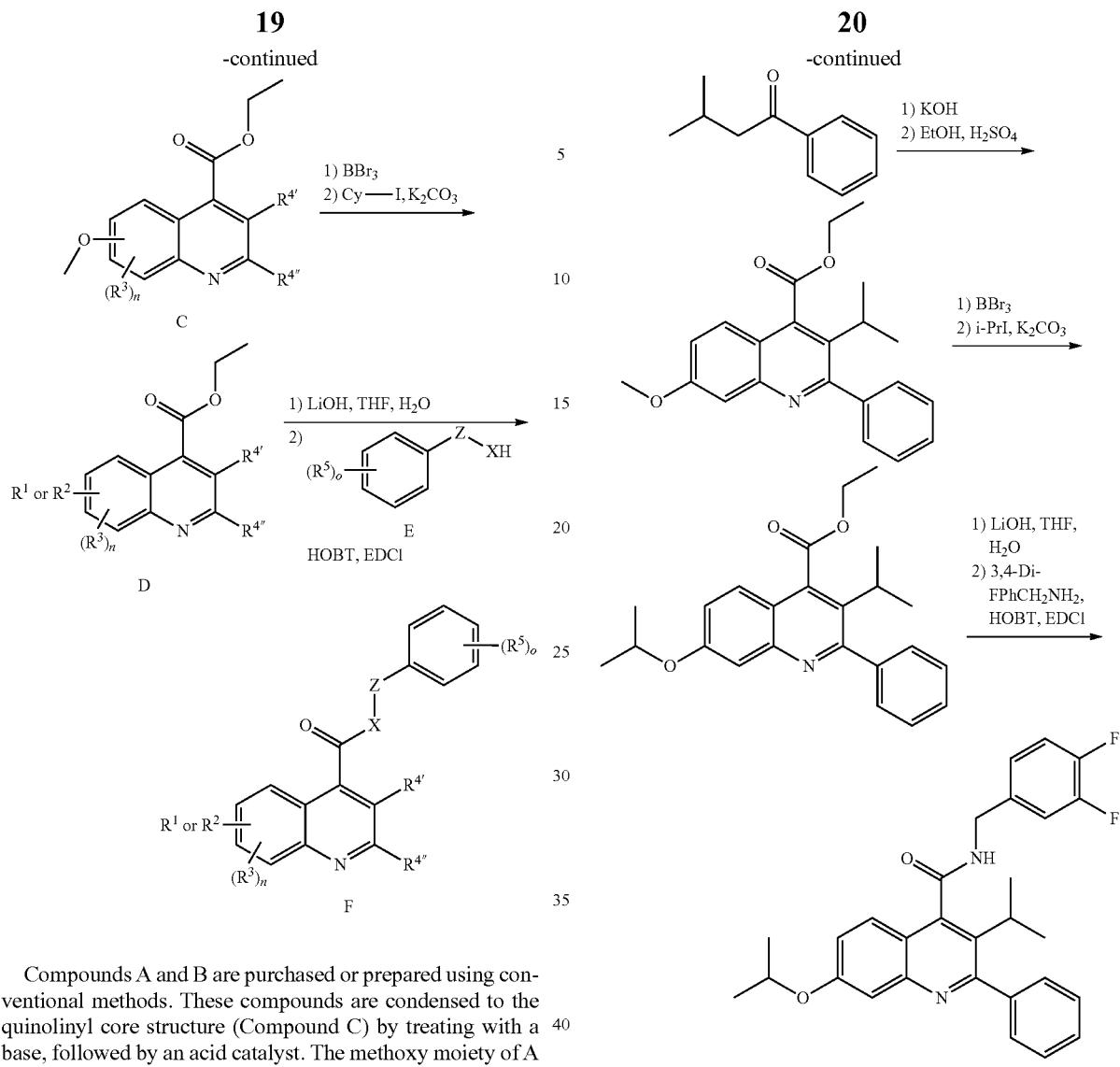

Compounds A and B are purchased or prepared using conventional methods. These compounds are condensed to the quinolinyl core structure (Compound C) by treating with a base, followed by an acid catalyst. The methoxy moiety of A and C acts as a precursor to either $R^1$ or $R^2$, depending upon which has the O-Cy structure. The methoxy is removed, and the Cy-moiety is added via a conventional nucleophilic substitution reaction to produce D. Alternatively, a protected nitrogen or sulfur atom may be used to yield the —S-Cy, or —NH-Cy moiety. The ester of D is then cleaved and added to E to obtain the final compound F.

The naphthyl analog of C may be prepared by oxidizing the corresponding hydroxyl naphthaldehyde and adding E as in Scheme 1. Methods of preparing these compounds are known, for example, Chamontin, et. al. (Tetrahedron 55 (1999) 5821-5830) provides a method that may be used.

One hypothetical example of use of the method of Scheme 1 is depicted in Scheme 2 below.

Scheme 2

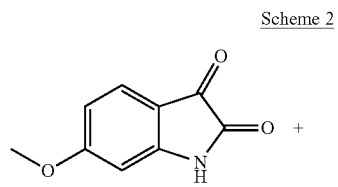

These compounds may be assessed for their ability to activate or block activation of the human S1P3 receptor in T24 cells stably expressing the human S1P3 receptor by the following procedure. Ten thousand cells/well are plated into 384-well poly-D-lysine coated plates one day prior to use. The growth media for the S1P3 receptor expressing cell line is McCoy's 5A medium supplemented with 10% charcoal-treated fetal bovine serum (FBS), 1% antibiotic-antimycotic and 400 μg/ml geneticin. On the day of the experiment, the cells are washed twice with Hank's Balanced Salt Solution supplemented with 20 mM HEPES (HBSS/Hepes buffer). The cells are then dye loaded with 2 uM Fluo-4 diluted in the HBSS/Hepes buffer with 1.25 mM Probenecid and incubated at 37° C. for 40 minutes. Extracellular dye is removed by washing the cell plates four times prior to placing the plates in the FLIPR (Fluorometric Imaging Plate Reader, Molecular Devices). Ligands are diluted in HBSS/Hepes buffer and prepared in 384-well microplates. The positive control, Sphingosine-1-Phosphate (S1P), is diluted in HBSS/Hepes buffer with 4 mg/ml fatty acid free bovine serum albumin. The FLIPR transfers 12.5 μl from the ligand microplate to the cell plate and takes fluorescent measurements for 75 seconds, taking readings every second, and then for 2.5 minutes, taking readings every 10 seconds. Drugs are tested over the concentration range of 0.61 nM to 10,000 nM. Data for $Ca^{+2}$ responses are obtained in arbitrary fluorescence units and not translated into $Ca^{+2}$ concentrations. $IC_{50}$ values are determined through a linear regression analysis using the Levenburg Marquardt algorithm.

What is claimed is:

1. A compound of the formula:

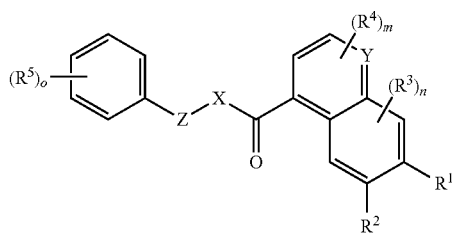

or a pharmaceutically acceptable salt thereof, wherein;
n is 0, 1, or 2;
m is 1 or 2;
o is from 0 to 5;
$R^1$ is selected from the group consisting of: —S-Cy, —NH-Cy, and —O-Cy, wherein Cy is selected from the group consisting of

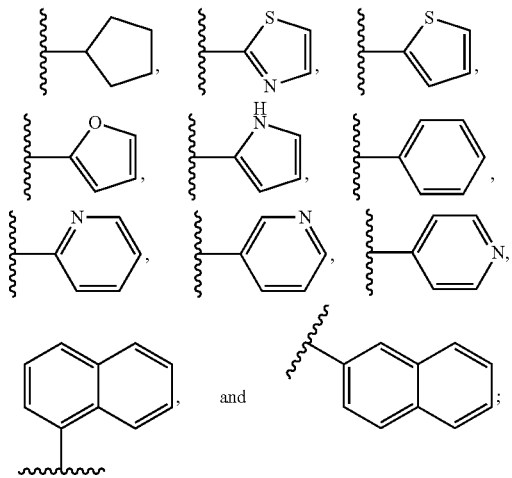

$R^2$ is hydrogen or a substituent of the formula $C_{0-12}H_{0-26}N_{0-2}O_{0-4}S_{0-1}P_{0-1}F_{0-6}Cl_{0-1}Br_{0-1}I_{0-1}$;
each $R^3$, $R^4$, and $R^5$ are independently a substituent of the formula $C_{0-12}H_{0-26}N_{0-2}O_{0-4}S_{0-1}P_{0-1}F_{0-6}Cl_{0-1}Br_{0-1}I_{0-1}$;
Y is N or C—H or C—$R^4$;
X is O, S, NH, N-alkyl having from 1 to 4 carbon atoms, or a bond; and
Z is hydrocarbyl of the formula $C_{1-8}H_{4-17}$.

2. The compound of claim 1 wherein $R^2$, $R^3$, $R^4$, and $R^5$ are moieties having no Cl, Br, or I, unless the Cl, Br, or I is attached directly to a carbon of an aromatic ring.

3. The compound of claim 2 wherein $R^2$ is selected from the group consisting of H, methyl, CHO, $CO_2H$, $COCH_3$, F, Cl, Br, OH, SH, $SCH_3$, $OCH_3$, $NH_2$, and $NO_2$; and each of $R^3$ and $R^5$ is independently selected from the group consisting of methyl, CHO, $CO_2H$, $COCH_3$, F, Cl, Br, OH, SH, $SCH_3$, $OCH_3$, $NH_2$, and $NO_2$.

4. The compound of claim 1 wherein Z is —$CH_2$—.

5. The compound of claim 1 wherein Y is CH.

6. The compound of claim 1 wherein Y is N.

7. The compound of claim 1 wherein X is O.

8. A compound of the formula:

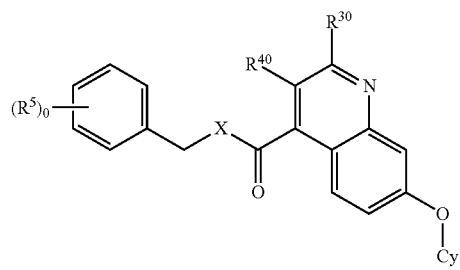

or a pharmaceutically acceptable salt thereof, wherein:
$R^{30}$ is phenyl, heteroaryl, or t-butyl;
$R^{40}$ is $C_{1-6}$ alkyl, $C_{1-7}$ carboxylate, or $C_{1-7}$ alkylcarbonyl; and
Cy is a substituted or unsubstituted carbocycle or a substituted or unsubstituted heterocycle.

9. The compound of claim 8 wherein X is NH.

10. The compound of claim 8 wherein $R^{30}$ is phenyl.

11. The compound of claim 10 of the formula:

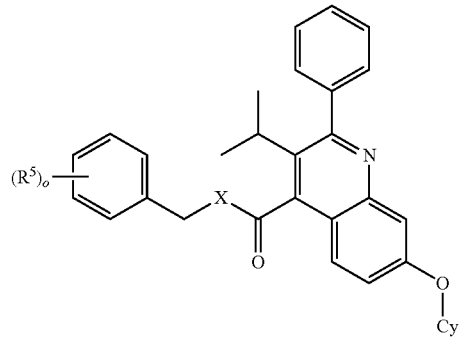

or a pharmaceutically acceptable salt thereof.

12. The compound of claim 11 selected from the group consisting of:

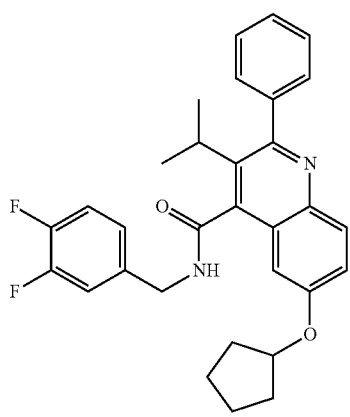
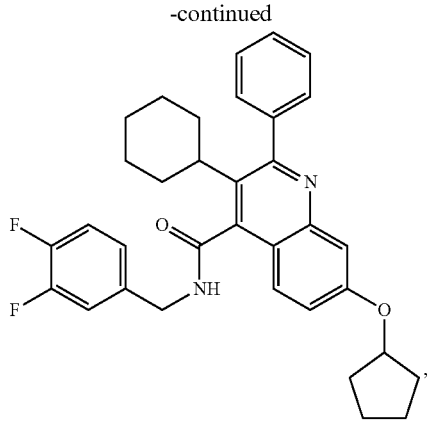
and
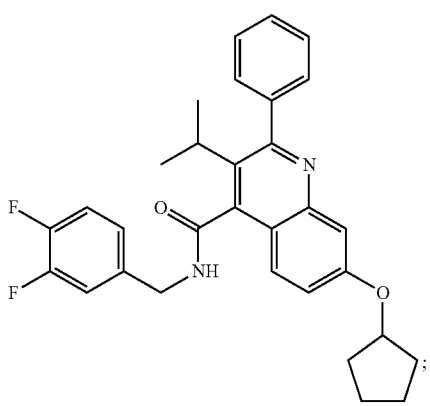
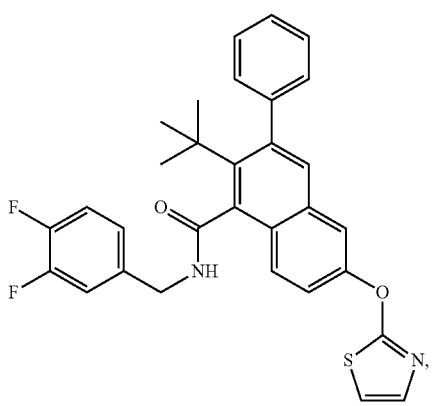
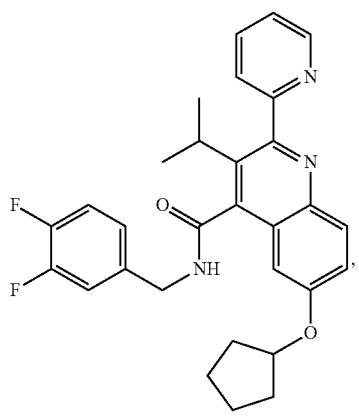
or a pharmaceutically acceptable salt thereof.
13. The compound of claim 1 wherein Z is $C_{1-8}$ alkyl.
14. A compound selected from the group consisting of
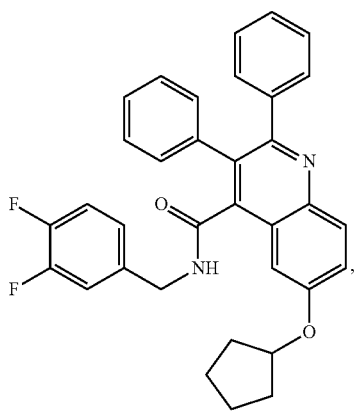
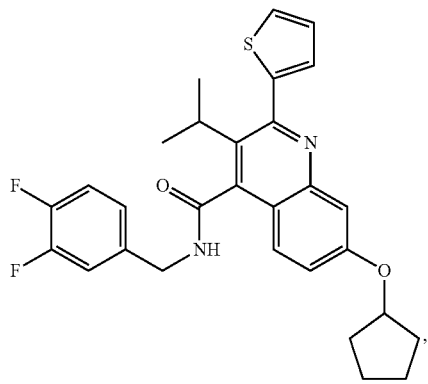

25
-continued
26
-continued
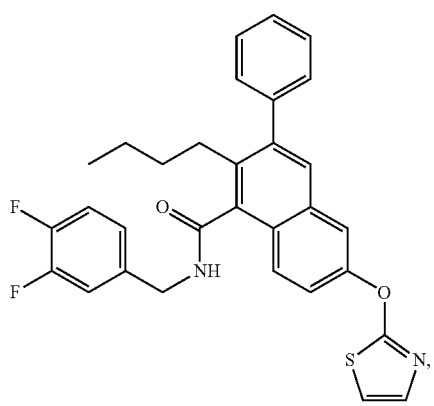
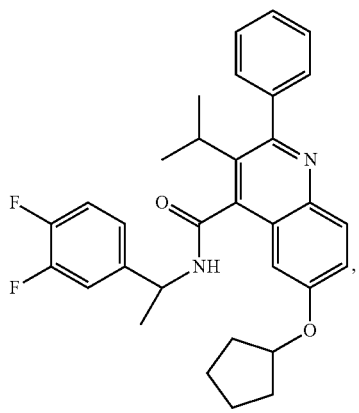

27
-continued
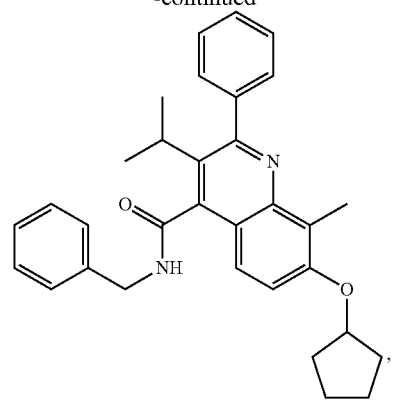
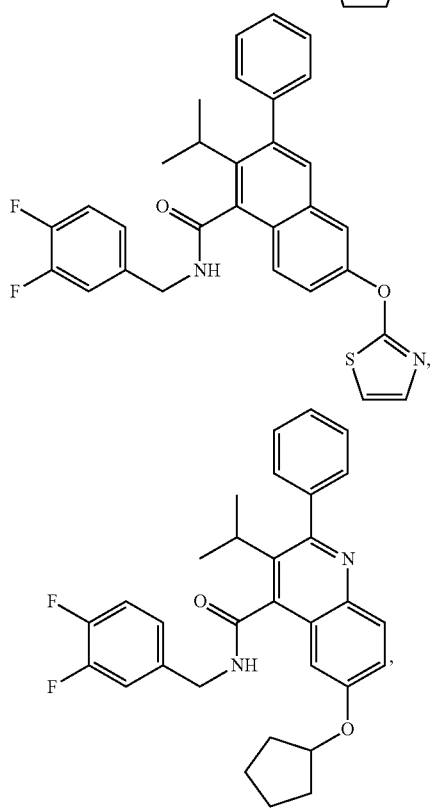
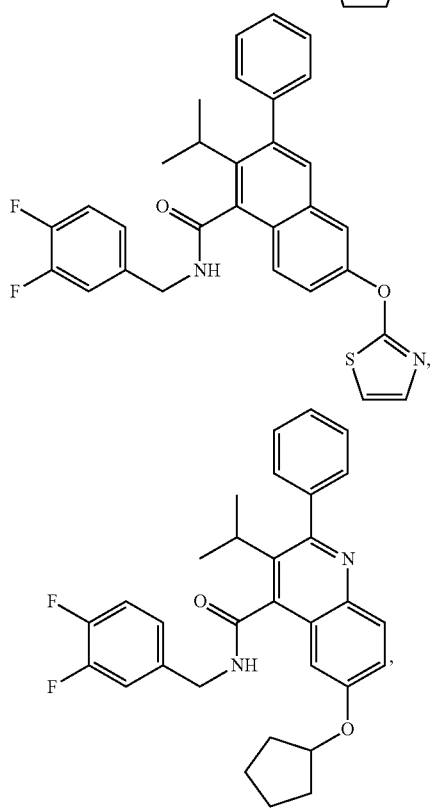
28
-continued
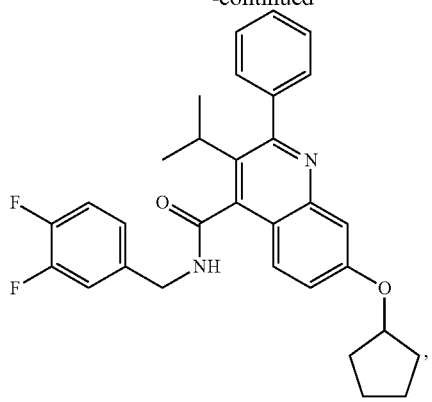
and
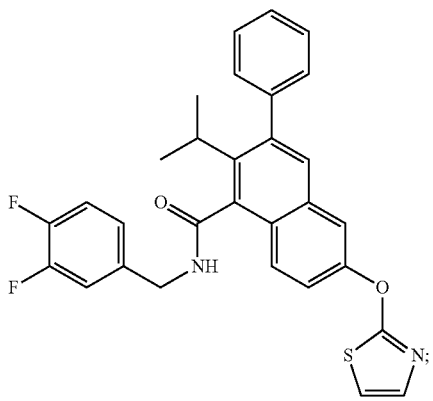
or a pharmaceutically acceptable salt thereof.
* * * * *